United States Patent [19]

Aiache et al.

[11] Patent Number: 5,766,619
[45] Date of Patent: Jun. 16, 1998

[54] PHARMACEUTICAL DOSAGE FORM FOR OCULAR ADMINISTRATION AND PREPARATION PROCESS

[76] Inventors: Jean-Marc Aiache, 17 rue du Maréchal Galliéni; Gilbert Serpin, 30 rue Rameau, both of 63000 Clermont-Ferrand, France

[21] Appl. No.: 331,603
[22] PCT Filed: May 4, 1993
[86] PCT No.: PCT/FR93/00433
§ 371 Date: Nov. 4, 1994
§ 102(e) Date: Nov. 4, 1994
[87] PCT Pub. No.: WO93/21901
PCT Pub. Date: Nov. 11, 1993

[30] Foreign Application Priority Data

May 5, 1992 [FR] France .................. 92 05514

[51] Int. Cl.[6] .................. A61K 9/36; A61K 9/42; A61M 31/00; A61F 2/00
[52] U.S. Cl. .................. 424/427; 424/464; 424/476; 424/480; 424/486; 424/487; 424/488; 514/786
[58] Field of Search .................. 424/427, 428, 424/464, 480, 486, 487, 488, 476; 514/786

[56] References Cited

U.S. PATENT DOCUMENTS

| | | | |
|---|---|---|---|
| 3,630,200 | 12/1971 | Higuchi | 128/260 |
| 3,828,777 | 8/1974 | Ness | 128/260 |
| 3,863,633 | 2/1975 | Ryde et al. | 128/260 |
| 3,986,510 | 10/1976 | Higuchi et al. | 424/19 |

FOREIGN PATENT DOCUMENTS 2140114  12/1973  France .

OTHER PUBLICATIONS

Handbook of Pharmaceutical Excipients, Second Edition, 1994, pp. 211, 229 & 231, 362–366, and 2249.

Primary Examiner—James M. Spear
Attorney, Agent, or Firm—Pollock, Vande Sande & Priddy

[57] ABSTRACT

An insoluble pharmaceutical dosage form for ocular administration including a matrix including at least one polymer and at least one active ingredient and a first layer of glycerides distributed at least over a surface of the matrix. The dosage form is an insoluble solid tablet.

36 Claims, 1 Drawing Sheet

TABLETS OF BATCH 5

PHARMACEUTICAL DOSAGE FORM FOR OCULAR ADMINISTRATION AND PREPARATION PROCESS

This application is a 371 PCT/FR 93/00433 filed May 5, 1993.

FIELD OF THE INVENTION

The present invention relates to pharmaceutical dosage forms intended for the ocular administration of active ingredients that it is desired to deliver in a more or less prolonged fashion, as well as to a process for preparing the dosage forms.

BACKGROUND OF THE INVENTION

The entry of active ingredients into the eye takes place essentially via the conjunctiva, which is highly vascularized. Entry via the cornea is hotly disputed; it is considered to be very selective and influenced by many factors. The epithelium is considered to play the part of a barrier.

The secretion and drainage of the lacrimal fluid bring about a rapid elimination of all conventional medicinal dosage forms applied to the surface of the eye. In the case of eyewashes, 20% of the drop instilled may be retained by the eye, and five minutes after administration only 8% of the 20% remains in the conjunctival cul-de-sac. This is due to the renewal of lacrimal fluid, which can be enhanced as a result of the irritation caused by the drop. The outcome of this brief contact time, or else of binding to proteins, is that only a small fraction enters the eye. Conventional means such as increasing the viscosity of the eyewashes, the addition of surfactants, oily solutions or ointments are relatively ineffective.

In addition to prolonging the action, the new technologies developed in recent years seek to provide other advantages, such as a steady concentration of active principles in the lacrimal fluid for a more sustained pharmacological response, a decrease in side effects and a less exacting dosage regimen, which should improve patient compliance.

With this aim in view, insoluble extraocular implants of the Ocusert® type appeared in 1973 in the USA. They take the form of two insoluble, crimped semipermeable membranes containing the solution of medicinal active principles that, over a few days, are released slowly into the conjunctival cul-de-sacs. However, this type of product gives rise to many problems of tolerance that limit their use.

Extraocular implants then underwent development. They form the subject of a Pro-Pharmacopea monograph in April-May 1988 (No. 500) under the name of ophthalmic insert. Hitoschi Ozawa (Biomaterials, vol. 4, July 1983) studied the value of ocular inserts impregnated with antibiotics (including erythromycin) in the treatment of trachoma in rabbits, and their behavior in vitro. Despite their satisfactory activity in vivo, soluble or biodegradable inserts have, however, the drawback of being able to leave debris and of giving rise to disorders of vision resulting from dissolution of the polymer. For this reason, their use in the context of a surgical procedure seems to be ruled out.

SUMMARY OF THE INVENTION

The use of an insoluble solid dosage form capable of being readily removed from the eye after releasing the active principles would be preferable. In addition, for some surgical operations on the eye, it is necessary to maintain the eye in a state of mydriasis and cycloplegia for several hours or even days.

Thus, the subject of the present invention is a pharmaceutical dosage form intended for ocular administration, characterized in that it possesses, from the inside to the outside:

a matrix consisting of at least one polymer and containing at least one active ingredient.

a first layer of glycerides.

DETAILED DESCRIPTION OF THE INVENTION

Figure 1:
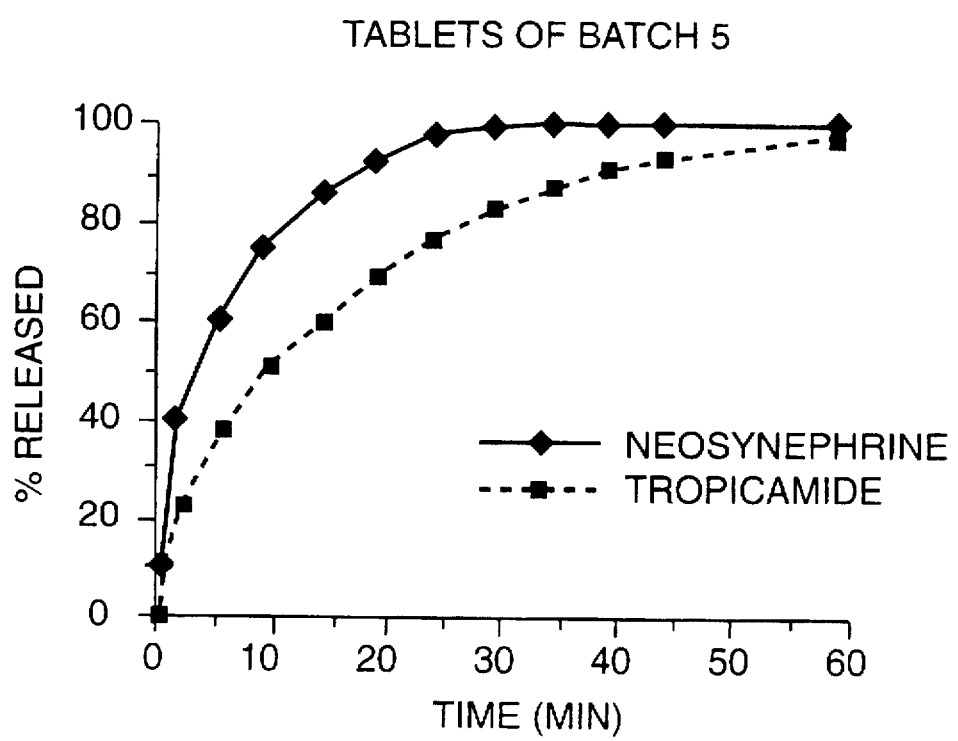
FIG. 1 shows a curve of cumulative percentages of active ingredient released for tablets of Formula 5, in relation to time.

The polymer or polymers constituting the matrix of the present invention form a network that confines the molecules of active principle and release them gradually. A portion of the glycerides forming the first layer of coating can be present within the matrix. They provide for a lubricant role during tabletting. The amount thereof is adjusted so that they distribute at the surface of the core and form an even and homogeneous layer, of variable thickness in accordance with the rate of release of the active principle that is desired.

The central core of the pharmaceutical dosage form can also contain the excipients needed for its formulation and that are known to a person skilled in the art, such as a suitable wetting agent, binding agent and diluent.

The polymer(s) used for the matrix is chosen, in particular, from the group comprising polyethylene, acrylic polymer, polyvinyl chloride, cellulose derivatives of the HPMC type, polyvinyl alcohol and Eudragit®.

The Eudragits are a family of acrylic resin type compounds marketed by Rö hm Pharma GmbH.

Solid glycerides are understood to mean glycerides occurring either as powder, or in liquid form adsorbed onto carriers. Natural or semisynthetic glycerides are preferably used, especially triglycerides. Compritol®, or glycerye benhydrate, may be mentioned, for example.

According to one of the aspects of the invention, the pharmaceutical dosage form possesses, in addition, a second layer, forming a semipermeable outer membrane.

This outer membrane has a dual function. On the one hand, in playing the part of a dialyzing barrier, it permits better control of the rate of release of the active principle or principles present in the matrix structure of the core.

On the other hand, this coating improves the tolerability of the pharmaceutical dosage form in vivo, and, hence, permits prolonged maintenance without the side effects of irritation observed with traditional inserts.

The second layer is formed from a thermoplastic derivative of cellulose, for example ethylcellulose or cellulose acetate. A person skilled in the art is in a position to choose any other compound capable of providing for the functions of a semipermeable membrane.

The pharmaceutical dosage form according to the invention is preferably a tablet that can be placed in the patient's conjunctival cul-de-sac so as to release the active principles gradually therein.

Advantageously, its dimensions are between approximately 2.5 and 4 mm in length and between approximately 1 and 3 mm in diameter.

Such tablets have optimal properties with respect to qualitative composition, size and robustness of the tablets.

These dosage forms can be positioned and removed readily from the conjunctival cul-de-sac without leaving debris.

Preferably, the pharmaceutical dosage forms according to the invention contain at least one active ingredient chosen from the group comprising mydriatics, antibiotics and anti-inflammatories.

According to one of the aspects of the invention, tablets of elongated shape are prepared, containing, in the central matrix, two mydriatics acting according to a different mechanism, neosynephrine and tropicamide.

Neosynephrine, used in the form of its hydrochloride, is an alpha-adrenergic stimulant used as a decongestant vasoconstrictor and mydriatic.

Tropicamide is a parasympatholytic of the antimuscarinic family, which blocks acetylcholine receptors, chiefly those of the iris sphincter and ciliary muscles; it is used clinically in the treatment of uveitis in order to obtain cycloplegia, in particular for surgery on the lens.

The combination of these two active principles enables a synergy to be observed. Such tablets, after sterilization with gamma rays, may be placed for 1 to 2 hours in the conjunctival cul-de-sac of patients in the preoperative situation, and then removed immediately before surgery of the eye which has been brought into a fit state.

Preferably, in the pharmaceutical dosage form according to the invention, the active ingredient is present at a level of between 1 and 60%, the polymer of the matrix is present at a level of between 25 and 70%, and the glycerides are present at a level of 8 to 40%, relative to the total weight of the tablet.

The subject of the present invention is also a process for preparing a pharmaceutical dosage form having one or more of the features defined above. The process includes performing the following steps:

a) mixing of the active ingredient or ingredients with the polymer or polymers constituting the matrix, b) optionally, granulation of the mixture obtained after wetting and incorporation of adjuvants, c) addition of the glycerides and mixing, d) direct tabletting of the mixture obtained at the end of the preceding step.

The mixing of the active ingredient or ingredients with the polymers and possible adjuvants must be sufficiently homogeneous for the glycerides to distribute inside and outside the tablet on tabletting; to this end, granulation will optionally be performed before adding the glycerides.

According to one of its aspects, the process according to the invention is characterized in that, after step (d), a step of coating the tablet with a thermoplastic derivative dissolved in an organic solvent is performed.

This additional step enables the second layer or dialyzing membrane to be formed.

The coating can, in particular, be performed in a turbo-mixer or on an air-fluidized bed.

Ethylcellulose is, for example, used in aqueous-alcoholic solution, and drying is carried out on an air-fluidized bed.

For the purpose of their use, these tablets are then sterilized, preferably by gamma radiation.

Other features and advantages of the present invention will become more clearly apparent on reading the examples that follow, which are in no way intended to limit its scope.

EXAMPLE 1

Different pharmaceutical dosage forms according to the invention are prepared by the following method:

Neosynephrine taken the form of small crystals. Since these tablets are intended for ophthalmic use, it is necessary to have very fine powders at one's disposal. Neosynephrine hydrochloride is, hence, ground beforehand, contrary to tropicamide, the powder of which is sufficiently fine. The active ingredients are then sieved through a sieve of mesh 0.400 mm, as are the excipients of the internal and external phase.

The active ingredients and the excipients are then weighed and mixed in a Turbula mixer for ten minutes.

Wetting of the powder mixture is carried out in a Kenwood apparatus, followed by granulation on a 1-mm screen. The particles obtained are dried in a ventilated oven for 4 hours at 45° C., before being sized on a 0.630-mm screen for the formulae 1, 2 and 3 and 0.315-mm screen for the formulae 4, 5 and 5', for reasons explained later. The particles are then weighed and mixed with the external phase.

The last step consists of a direct tabletting on an alternating machine.

FORMULAE
* Formula 1

| | Unit formula for m = 25 mg |
|---|---|
| Tropicamide: 2.5% | 0.625 mg |
| Neosynephrine: 50% | 12.500 mg |
| Ethylcellulose N10: 42.5% | 10.625 mg |
| COMPRITOL: 5% | 1.250 mg |
| Distilled water: Q.S. | |
| | 25.000 mg |

- COMPRITOL is used in the external phase as a direct tabletting lubricant.
- A portion of the ethylcellulose and the water are used for wetting, the remainder of the ethylcellulose has the role of a binding agent.

* Formula 2

| | Unit formula for m = 25 mg |
|---|---|
| Tropicamide: 0.25% | 0.0625 mg |
| Neosynephrine: 50% | 12.5000 mg |
| EUDRAGIT RLPM: 41.15% | 10.2875 mg |
| EUDRAGIT NE30D: 3.6% | 0.9000 mg |
| COMPRITOL: 5% | 1.2500 mg |
| | 25.0000 mg |

- EUDRAGIT RLPM is used here as a binding agent, and serves to make the matrix.
- EUDRAGIT NE30D is employed as wetting liquid.
- COMPRITOL serves in the external phase (lubricant).

* Formula 3

| | Unit formula for m = 25 mg |
|---|---|
| Tropicamide: 0.20% | 0.050 mg |
| Neosynephrine: 49.8% | 12.450 mg |
| EUDRAGIT RLPM: 38.4% | 9.600 mg |
| EUDRAGIT NE30D: 3.6% | 0.900 mg |
| COMPRITOL: 8% | 2.000 mg |
| | 25.000 mg |

* Formula 4

| Unit formula for m = 12.5 mg | |
|---|---|
| Tropicamide: 2.5% | 0.3125 mg |
| Neosynephrine: 50% | 6.2500 mg |
| EUDRAGIT RLPM: 35.9% | 4.4875 mg |
| EUDRAGIT NE30D: 3.6% | 0.4500 mg |
| COMPRITOL: 8% | 1.0000 mg |
| | 12.5000 mg |

- For the first batch of the Formula 4, the particles were granulated on 0.630-mm screen. However, the punches are half the size in this case as for the above formulae. The tabletting chamber is reduced by one half and the particles proved too large for a good packing of the matrix. Hence the particles were sized on a 0.315-mm screen, and the particles thus reduced, permitted good tabletting.

For the first batch of the Formula 4, the particles were granulated on 0.630-mm screen. However, the punches are half the size in this case as for the above formulae. The tabletting chamber is reduced by one half and the particles proved too large for a good packing of the matrix. Hence the particles were sized on a 0.315-mm screen, and the particles thus reduced, permitted good tabletting.

| *Formula 5 | |
|---|---|
| Unit formula for m = 11.2 mg | |
| Tropicamide: 2.5% | 0.2800 mg |
| Neosynephrine: 48% | 5.3760 mg |
| EUDRAGOT RLPM: 35.9% | 4.0208 mg |
| EUDRAGIT NE30D: 3.6% | 0.4032 mg |
| COMPRITOL: 10% | 1.1200 mg |
| | 11.2000 mg |

The punches used are the same as for the Formula 4, and the particles are calibrated on a screen of mesh 0.315 mm. Formula 5'

This is the same formula as the Formula 5', but the 11.2-mg tablets obtained are then coated with a 10% aqueous-alcoholic solution of ethylcellulose.

The coating solution is prepared the day before and stirred all night long. It has the following formula:

950° strength alcohol: 90 ml ethylcellulose: 10 g

The tablets are dipped one by one using a small strainer, five times in succession; between each dip, they are dried placed on nonwoven paper in an oven at 50° C.

The proportions in these tablets before coating are the same as those in the Formula 5.

EXAMPLE 2

The kinetics of release of the active principles were studied by the following technique.

The tablet is placed in a hermetically sealed plastic tube of capacity 20 ml and filled with 20 ml of 0.9% NaCl solution. The tube is then attached to the stirrer system of the Rotating-Bottle in vitro dissolution apparatus (described in the National Formulary XV) and stirred at a constant speed of 20 rpm. The assembly is placed in an oven at 37° C. One tenth of the liquid (namely 2 ml) is then sampled at specified times and replaced by the same amount of fresh solvent (0.9% NaCl). The sampling times are: 2, 6, 10, 15, 20, 25, 30, 35, 40, 45, 60 minutes. The samples are then analyzed by HPLC.

The cumulative percentages released in vitro are described by a curve with the time as abscissa and the percentages released as ordinates.

For the tablets corresponding to the Formula 5, the cumulative percentages on neosynephrine released in vitro in terms of time are collated in Tables 1 and 2, and the curve obtained shown in FIG. 1.

TABLE 1

| Time (minutes) | Tablet no. 1 | Tablet no. 2 | Tablet no. 3 | Mean (%) | Standard deviation |
|---|---|---|---|---|---|
| 2 | 43.8 | 37.3 | 40.2 | 40.4 | 2.7 |
| 6 | 58.4 | 58.8 | 65.3 | 60.8 | 3.2 |
| 10 | 74.7 | 73.9 | 75.8 | 74.8 | 0.8 |
| 15 | 83.1 | 85.3 | 88.4 | 85.6 | 2.2 |
| 20 | 90.4 | 94.1 | 95.0 | 93.2 | 2.0 |
| 25 | 95.5 | 98.2 | 100 | 97.9 | 1.8 |
| 30 | 98.2 | 100 | 100 | 99.4 | 0.8 |
| 35 | 100 | 100 | 100 | 100 | 0 |
| 40 | 100 | 100 | 100 | 100 | 0 |
| 45 | 100 | 100 | 100 | 100 | 0 |
| 60 | 100 | 100 | 100 | 100 | 0 |

TABLE 2

| Time (minutes) | Tablet no. 1 | Tablet no. 2 | Tablet no. 3 | Mean (%) | Standard deviation |
|---|---|---|---|---|---|
| 2 | 25.1 | 21.7 | 21.6 | 22.8 | 1.6 |
| 6 | 39.1 | 34.4 | 40.2 | 37.9 | 2.5 |
| 10 | 53.4 | 47.9 | 51.7 | 51.0 | 2.3 |
| 15 | 61.4 | 57.7 | 64.3 | 61.1 | 2.7 |
| 20 | 69.5 | 66.7 | 72.9 | 69.7 | 2.5 |
| 25 | 77.1 | 73.4 | 80.9 | 77.1 | 3.1 |
| 30 | 82.2 | 77.6 | 86.5 | 82.1 | 3.6 |
| 35 | 90.4 | 80.7 | 89.6 | 86.9 | 4.4 |
| 40 | 92.7 | 85.1 | 94.5 | 90.8 | 4.1 |
| 45 | 95.0 | 88.0 | 98.7 | 93.9 | 4.4 |
| 60 | 100 | 93.7 | 100 | 97.9 | 3.0 |

EXAMPLE 3

Study in rabbits

The aim is to determine objectively in rabbits the possible irritant properties and the mydriatic effect (the time-point of onset of mydriasis and its progression over time) caused by the tablets on single administration thereof in the rabbit's eye. The administration consists of placing one of these dosage forms in the rabbit's conjunctival cul-de-sac.

1. Study Protocol

Species

New Zealand Albino rabbits, originating from a specialized breeding station, that weigh between 1.5 kg and 2.5 kg.

The animals are identified individually by tattooing the ear.

Housing

The animals are housed in cages of standardized size. The cages are placed in an air-conditioned animal house (17°–21° C.), maintained at an atmospheric moisture concentration of between 45 and 65% relative humidity except during the hours of cleaning, during which the unrecycled filtered air is renewed. The nychthemeral cycle is artificially re-created under the following conditions: 12 hours of light/12 hours of darkness.

Feeding

V.A.R. 112 feeds.

Drinking water

Municipal tap water is distributed ad libitum in propylene feeding bottles with a stainless steel nipple.

Observation of animals

This observation is performed by direct inspection. After the tablet has been placed in the conjunctival cul-de-sac, the eyelids are closed for approximately 10 seconds in order to prevent rejection of the tablet. Only the left eye of the rabbit is treated, the right eye serves as control. During treatment, the animals are maintained for 1 hour in a restraining box so that they cannot rub the eye, and they are then replaced in the cage after removal of the tablet using a forceps. However, for the formulae 1 and 2, the animals were maintained for a further hour in the restraining box after removal of the dosage form, for easier observation of the mydriasis. However, in view of the poor tolerance of the rabbits to the treatment, this 1-hour extension in the restraining box was not retained for the other batches of tablets.

The various features of ocular irritation and the various stages of mydriasis are quantified by scoring, and will be assessed here with the naked eye.

Ocular lesions

The various features and their scoring described below are those defined in the working procedure.

| a) Chemosis (swelling) | |
|---|---|
| No swelling | S-0 |
| Slight swelling, including of the nictitating membrane | S-1 |
| Swelling with eversion of the eyelid | S-2 |
| Swelling with eyelids half closed | S-3 |
| Swelling with eyelids more than half or completely closed | S-4 |
| b) Watering | |
| No watering | W-0 |
| Slight watering | W-1 |
| Watering with moistening of the eyelids and the hairs in proximity to the eyelids | W-2 |
| Watering with moistening of the eyelids and the hairs over broad areas of the eye | W-3 |
| c) Reddening of the palpebral conjunctive | |
| Normal vessels | V-0 |
| Vessels markedly more injected than normal | V-1 |
| Vessels difficult to distinguish individually diffuse bright red color | V-2 |
| dark red color | V-3 |
| d) Corneal lesion Degree of opacification: | |
| No visible modification or loss of shine in sunlight | O-0 |
| Presence of translucent areas (diffuse or disseminated), details of the iris clearly visible | O-1 |
| Presence of a readily identifiable translucent area, details of the iris slightly masked | O-2 |
| Presence of an opalescence, no detail of the iris visible, contour of the pupil barely discernable | O-3 |
| Presence of a total corneal opacity rendering the iris and pupil invisible | O-4 |

Stages of mydriasis:

M-1: Beginning of mydriasis, the pupil is slightly more dilated relative to the untreated eye M-2: Moderate mydriasis M-3: Maximal mydriasis 2. Results Appearance of the formulation The various states of the tablets observed after withdrawal are in agreement with the in vitro tests carried out previously. In effect, the tablets of the formula 1, placed in a crystallizing dish with distilled water, rapidly become friable and, in vivo, on removing them from the rabbits' eye, they disintegrate leaving debris. The tablets of the formula 2 remain whole and are merely softened by contact with the lacrimal fluid. Subsequently, an improvement in the hardness of these tablets was sought so as to be able to remove them more readily and without debris. These objectives were achieved with the formula 5, and formula 5' which includes the presence of a coating.

ACTIVITY OF THE TABLETS

Formula 1

The proportion of neosynephrine in these tablets is very close to that of the $LD_{50}$ in rats (dose for which, after single administration, one half of the animals treated die) with subcutaneous administration. These dosage forms were, none the less, administered to rabbits in order to find out whether the active principles are released in vivo and to endeavor to assess the extent of their activity. A flash mydriasis is obtained, which rapidly becomes collateral, maximal in less than 10 minutes. The rabbits display, less than one hour later, considerable signs of overdosage, and die shortly after removal of these dosage forms, hence less than 2 hours after their administration. There has, hence, been an almost immediate release of the active principles, followed by passage into the systemic circulation, as compared with an intravenous route.

Formula 2

Though subjected to one tenth the dose of tropicamide, the rabbits of batch 2 were unable to withstand the still considerable dose of neosynephrine. The mydriatic effect was less violent, and one rabbit out of three survived. At around the 4th hour, the collateral mydriasis disappears and the mydriasis of the treated eye, though good, is no longer maximal. The dosage is still too strong and the rabbits display many signs of overdosage.

Formula 4

These tablets contain much smaller doses of neosynephrine, the proportion of which is reduced by more than 50%. Tolerance is markedly improved, since the rabbits no longer display visible adverse effects. The much more gradual mydriatic effect is no longer collateral. The mydriasis passes through two intermediate stages, M-1 and M-2, before being maximal, approximately 25 minutes after insertion of the tablet. The mydriatic effect is stable over at least 5 hours.

Formula 5 and 5'

For these tablets, the kinetics of the mydriatic effect are slowed down still further: maximal mydriasis is obtained shortly before 30 minutes. Tolerance is excellent after administration of the coated tablets of the formula 5', with which the rabbits do not appear to be in any way effected by the treatment. The coating is considered to play the part of a matrix holding up the release of the neosynephrine and tropicamide. These observations correlate with the in vitro kinetics described above. Mydriasis remains good for at least 4 hours after administration of these tablets.

Ocular lesions

As a result of their size and consistency, the tablets of batch 1 cause a large amount of irritation, in particular considerable watering. The vessels of the palpebral conjunctiva are slightly more injected than normal and the eyelids are somewhat swollen. After removal of the tablets, these signs disappear; they seem to be due in large parts to the presence of these tablets in the conjunctival cul-de-sac.

The tablets of the other formulae produce only slight watering in general. Rabbits that have had the coated tablets display no sign of irritation. This good tolerance is considered to be due to the small size of the tablets, their hardness and their smoother appearance. Furthermore, the active ingredients appear to be released much more gradually than with the other tablets of the previous formulae.

EXAMPLE 4

Study in man

Trials are performed under medical supervision by a clinician according to an established protocol.

1. Study Protocol

The study took place on 8 subjects; 4 received the tablets of the formula 5, the other 4 those of the formula 5'. Only one tablet was administered to each patient, the untreated second eye served as control.

The clinical observations reported by the doctor, including the state of mydriasis, local reactions and possible side effects, as well as the state of the tablet after removal, are described in Table A for the tablets of the formula 5. The detailed observations for each subject after administration of the tablets of the formula 5' have not been recorded since the results proved identical in all 4 cases. The clinician has hence given a description of the general state of the 4 subjects.

Each patient is assigned the number 1, 2, 3 or 4.

2- Results

Results obtained after administration of the tablets of the formula 5:

The clinical observations are described in Table A below.

TABLE A

| Obs.* no. | State of mydriasis | Local reaction | Side effects |
|---|---|---|---|
| 1 | excellent | nil | none |
| 2 | acceptable | petechiae | none |
| 3 | excellent | very pronounced sulcus, petechiae | none |
| 4 | excellent | nil | none |

*Obs = Observation

For all four subjects, as a result of the relatively smooth surface of the tablets, they slide easily into the conjunctival cul-de-sac. However, the edges of the tablets are sharp, and this partly explains the hemorrhagic petechiae. The size of the tablets is considered to be ideal. After 30 minutes, the tablet is very soft; it nevertheless remains whole on withdrawal, which takes place almost spontaneously by simply pressing on the rim of the lower eyelid. The doses of the mydriatic product appear to be correct.

Results obtained after administration of the tablets of the formula 5':

The results listed below are identical for all 4 subjects.

Mydriasis is excellent after 20 minutes,

Impression at the conjunctival site, with a few very fine hemorrhagic petechiae. No edematous reaction.

No general neurovegetative reaction was reported

Hence the coating appears to be effective, in effect there is no debris.

We claim:

1. An insoluble pharmaceutical dosage form for ocular administration, comprising:

a matrix including at least one polymer including at least one member selected from the group consisting of polyethylene, acrylic polymers, polyvinyl chloride, hydroxpropylmethylcellulose, polyvinylalcohol, and polymeric methacrylates and at least one active ingredient; and a first layer of glycerides distributed at least over the surface of the matrix;

wherein the dosage form is an insoluble solid tablet.

2. An insoluble pharmaceutical dosage form according to claim 1, further comprising a second layer forming a semipermeable outer membrane.

3. An insoluble pharmaceutical dosage form for ocular administration, comprising:

a matrix including at least one polymer and at least one active ingredient; and a first layer of glycerides distributed at least over the surface of the matrix and present within the matrix;

wherein the dosage form is an insoluble solid tablet.

4. An insoluble pharmaceutical dosage form for ocular administration, comprising:

a matrix including at least one polymer and at least one active ingredient;

a first layer of glycerides distributed at least over the surface of the matrix; and a second layer forming a semipermeable outer membrane formed from a substituted thermoplastic cellulose compound selected from the groups consisting of ethers and esters;

wherein the dosage form is an insoluble solid tablet.

5. An insoluble pharmaceutical dosage form for ocular administration, comprising:

a matrix including at least one polymer and at least one active ingredient; and a first layer of glycerides distributed at least over the surface of the matrix;

wherein the dosage form is an insoluble solid tablet and wherein the dosage form includes by total weight of said dosage form between 1 and 60% of said active ingredient, between 25 and 70% of said polymer, and between 8 and 40% of said glycerides.

6. An insoluble pharmaceutical dosage form according to claim 1, wherein said glycerides are natural or semisynthetic solid glycerides.

7. An insoluble pharmaceutical dosage form for ocular administration, comprising:

a matrix including at least one polymer and at least one active ingredient, said polymer including at least one member selected from the group consisting of polyethylene, acrylic polymers, polyvinyl chloride, hydroxypropylmethylcellulose, polyvinylalcohol, and polymeric methacrylates;

a first layer of glycerides distributed at least over the surface of the matrix; and a second layer forming a semipermeable outer membrane;

wherein the dosage form is an insoluble solid tablet.

8. An insoluble pharmaceutical dosage form according to claim 2, wherein said semipermeable membrane is formed from a thermoplastic cellulose compound.

9. An insoluble pharmaceutical dosage form according to claim 2, wherein said semipermeable membrane is formed from a compound selected form the group consisting of ethylcellulose and cellulose acetate.

10. An insoluble pharmaceutical dosage form according to claim 1, wherein said active ingredient includes at least one member selected from the group consisting of mydriatics, antibiotics and anti-inflammatories.

11. An insoluble pharmaceutical dosage form according to claim 1, including by total weight of said dosage form between 1 and 60% of said active ingredient, between 25 and 70% of said polymer, and between 8 and 40% of said glycerides.

12. An insoluble pharmaceutical dosage form according to claim 1, wherein said dosage form is between approximately 2.5 and 4 mm in length and between approximately 1 and 3 mm in diameter.

13. A process for preparing an insoluble pharmaceutical dosage form, said process comprising the steps of:

a) mixing at least one active ingredient with at least one polymer, said active ingredient and said polymer comprising a matrix;

b) adding a first layer of glycerides over at least a surface of said matrix;

c) mixing said glycerides and said matrix to form a mixture; and d) forming said mixture into a tablet.

14. A process for preparing an insoluble pharmaceutical dosage form according to claim 13, further comprising the steps of:

wetting said mixture;

incorporating adjuvants into said mixture; and granulating said mixture.

15. A process for preparing an insoluble pharmaceutical dosage form according to claim 13, further comprising the step of:

coating the tablet with a second layer forming a semipermeable outer membrane.

16. A process for preparing an insoluble pharmaceutical dosage form according to claim 15 wherein said second layer is formed from a thermoplastic cellulose compound dissolved in an organic solvent.

17. A process for preparing an insoluble pharmaceutical dosage form according to claim 15, wherein said coating is performed by dipping the tablets in a solution of ethylcellulose in an organic solvent and said process further comprises the step of drying said coated tablets in an oven.

18. An insoluble pharmaceutical dosage form according to claim 1, wherein said first layer of glycerides is also present within the matrix.

19. A process according to claim 13, further comprising the step of:

adding said first layer of glycerides within said matrix.

20. An insoluble pharmaceutical dosage form according to claim 2, wherein said semipermeable membrane is formed from a substituted thermoplastic cellulose compound selected from the groups consisting of ethers and esters.

21. A process for preparing an insoluble pharmaceutical dosage form according to claim 15, wherein said second layer is formed from a substituted thermoplastic cellulose compound selected from the groups consisting of ethers and esters.

22. A process for preparing an insoluble pharmaceutical dosage form according to claim 15, wherein said second layer is formed from a compound selected from the group consisting of ethylcellulose and cellulose acetate.

23. An insoluble pharmaceutical dosage form according to claim 1, wherein said glycerides are triglycerides.

24. An insoluble pharmaceutical dosage form for ocular administration, comprising:

a matrix including at least one polymer and at least one active ingredient; and a first layer of natural or semisynthetic solid glyceryl behenate distributed at least over a surface of the matrix;

wherein the dosage form is an insoluble solid tablet.

25. The insoluble pharmaceutical dosage form according to claim 24, further comprising:

a second layer of a semipermeable membrane on at least one of said first layer and said matrix.

26. The insoluble pharmaceutical dosage form according to claim 24, wherein said semipermeable membrane is formed from a thermoplastic cellulose compound.

27. The insoluble pharmaceutical dosage form according to claim 7, wherein said dosage form is a tablet.

28. The insoluble pharmaceutical dosage form according to claim 7, wherein said glycerides are natural or semisynthetic solid glycerides.

29. The insoluble pharmaceutical dosage form according to claim 7, wherein said semipermeable membrane is formed from a thermoplastic cellulose compound.

30. The insoluble pharmaceutical dosage form according to claim 7, wherein said semipermeable membrane is formed from a compound selected from the group consisting of ethylcellulose and cellulose acetate.

31. The insoluble pharmaceutical dosage form according to claim 7, wherein said active ingredient includes at least one member selected from the group consisting of mydriatics, antibiotics and anti-inflammatories.

32. The insoluble pharmaceutical dosage form according to claim 7, including by total weight of said dosage form between 1 and 60% of said active ingredient, between 25 and 70% of said polymer, and between 8 and 40% of said glycerides.

33. The insoluble pharmaceutical dosage form according to claim 7, wherein said dosage form is between approximately 2.5 and 4 mm in length and between approximately 1 and 3 mm in diameter.

34. The insoluble pharmaceutical dosage form according to claim 7, wherein said first layer of glycerides is also present within the matrix.

35. The insoluble pharmaceutical dosage form according to claim 7, wherein said semipermeable membrane is formed from a substituted thermoplastic cellulose compound selected from the groups consisting of ethers and esters.

36. The insoluble pharmaceutical dosage form according to claim 7, wherein said glycerides are triglycerides.

\* \* \* \* \*